(12) United States Patent
Sugimoto (10) Patent No.: US 6,739,871 B2
(45) Date of Patent: May 25, 2004

(54) DENTITION IMAGE READING APPARATUS (75) Inventor: Yukiteru Sugimoto, Ohshima-gun (JP)

(73) Assignee: Orange House Co., Ltd., Yamaguchi-ken (JP)

( * ) Notice: Subject to any disclaimer, the term of this patent is extended or adjusted under 35 U.S.C. 154(b) by 268 days.

(21) Appl. No.: 10/001,138

(22) Filed: Oct. 23, 2001

(65) Prior Publication Data

US 2002/0058229 A1 May 16, 2002

(30) Foreign Application Priority Data

Oct. 25, 2000 (JP) ........................ 2000-325453

(51) Int. Cl.[7] .................................................. A61C 3/00
(52) U.S. Cl. .......................................... 433/29; 396/16
(58) Field of Search ....................... 433/29, 213, 214; 396/16; 600/109

(56) References Cited

U.S. PATENT DOCUMENTS

| | | | |
|---|---|---|---|
| 3,382,781 A | | 5/1968 | Hamilton |
| 3,812,505 A | | 5/1974 | Elliott |
| 4,935,635 A | * | 6/1990 | O'Harra |
| 6,402,707 B1 | * | 6/2002 | Ernst .......................... 600/590 |

FOREIGN PATENT DOCUMENTS

| | | |
|---|---|---|
| JP | 06-28859 | 8/1994 |
| JP | 09-140664 | 6/1997 |
| JP | 3056089 | 7/1998 |

OTHER PUBLICATIONS

WO 91/13586, Process and Device for Measuring the Dimensions of a Space, in Particular a Buccal Cavity, Publication Date Sep. 19, 1991.

* cited by examiner

*Primary Examiner*—Cary E. O'Connor
(74) *Attorney, Agent, or Firm*—Rankin, Hill, Porter & Clark LLP

(57) ABSTRACT

A dentition image reading apparatus (1) includes an in-mouth insert (11) to be inserted into mouth and image pick-up optics (21), the in-mouth insert including a light-transmitting portion (15) at least on one of front and back sides and a hollow portion (12) provided thereinside, the image pick-up optics (21) including: a light source (22) inserted in the hollow portion of the in-mouth insert for irradiating light on the dentition through the light-transmitting portion; a reflection mirror (23) for reflecting the light from the dentition toward the outside of the in-mouth insert; a scanner 31 for moving the light source and the reflection mirror along the depth direction of the hollow portion of the in-mouth insert; and an image pick-up optical system (41) for receiving the light reflected by the reflection mirror.

5 Claims, 9 Drawing Sheets

DENTITION IMAGE READING APPARATUS

BACKGROUND OF THE INVENTION

1. Field of the Invention

The present invention relates to a dentition image reading apparatus. More specifically, it relates to a dentition image reading apparatus for directly taking a picture of upper jaw dentition and lower jaw dentition from inside of mouth to obtain an entire image of the dentition.

2. Description of Related Art

Conventionally, a roentgenography has been widely used as an indispensable tool for obtaining image in dental medical treatment. However, in recent years, digital cameras and small CCD cameras have come to be used for the purpose of explaining to a patient.

For instance, an image pick-up device having a hand holder including an image sensor and optical fibers arranged in ring-shape around the image sensor has been proposed in Japanese Utility Model Application Publication No. Hei 6-28859.

In Japanese Patent Laid-Open Publication No. Hei 9-140664, a dental in-mouth observation camera having a light guide and a CCD sensor provided on a distal head of a hand piece has been proposed.

However, since the above apparatuses only partially take a picture of the tooth to be treated and the image of the entire dentition cannot be taken, a treatment-requiring portion, and relationship between the treatment-requiring portion and the normal portion cannot be recognized.

In order to obtain an image of the entire dentition, a "process and device for measuring the dimensions of a space, in particular a buccal cavity" disclosed in international Patent Publication No. WO91/13586, and a "dentition image reading apparatus" disclosed in Japanese Utility Model Registration No. 3056089 have been known.

In the former "measuring method of in-mouth space and an apparatus for implementing the method", a light beam from a light source is irradiated to a tooth in mouth through a deflecting device and the reflecting light from the tooth is transmitted to an image pick-up device through the deflecting device.

The latter "dentition image reading apparatus" accommodates an image sensor and a light source in a transparent container inserted in mouth and the dentition image is obtained while moving the image sensor and the light source within the transparent container.

However, former method for obtaining the entire image of the dentition, the "measuring method of in-mouth space and an apparatus for implementing the method", requires a deflecting device of complicated structure and production cost thereof is difficult to be reduced.

Further, since the latter "dentition image reading apparatus" accommodates the image sensor and the light source within the transparent container inserted into mouth, the size of the transparent container is increased and therefore is difficult to be used for a child.

SUMMARY OF THE INVENTION

An object of the present invention is to provide a dentition image reading apparatus capable of reducing size and cost thereof and capable of reading the entire image of the dentition with high accuracy. In order to achieve the above object, the dentition image reading apparatus according to the present invention includes following arrangement.

A dentition image reading apparatus according to the present invention includes: an in-mouth insert to be inserted in a mouth having an upper jaw dentition and a lower jaw dentition; and image pick-up optics, the in-mouth insert having a light-transmitting portion at least on one of front and back sides thereof and a hollow portion provided thereinside, the image pick-up optics having: a light source inserted in the hollow portion in the in-mouth insert for irradiating light on the dentition through the light-transmitting portion; a reflection mirror for reflecting the light from the dentition toward the outside of the in-mouth insert; a scanner for moving the light source and the reflection mirror along the depth direction of the hollow portion of the in-mouth insert; and an image pick-up optical system for receiving the light reflected by the reflection mirror.

According to the above arrangement, after inserting the in-mouth insert into mouth, the light source and the reflection mirror is positioned at a predetermined position in the hollow portion of the in-mouth insert by the scanner, where the light from the light source reaches to the dentition through the light-transmitting portion to be reflected by the dentition and, consequently reaches to the image pick-up optical system through the reflection mirror. In other words, the dentition image data of the line where the light source and the reflection mirror located is retrieved. Next, the light source and the reflection mirror are stopped by the scanner after a predetermined distance movement, the dentition image data at the position is retrieved. In the same manner, the light source and the reflection mirror are moved by a predetermined distance and the dentition image data at respective positions is retrieved, which is combined to obtain an entire image of the dentition.

Accordingly, the external shape, evenness, color and dimension of the tooth can be facilitated, which enables to determine treatment, record growth of a child, determine whether orthodontics is required or not, and determine whether orthodontics wiring is required or not in a quantitative manner, and further, enables to efficiently collect dentition image at a mass check-up.

Especially, since only the light source and the reflection mirror are accommodated in the hollow portion of the in-mouth insert to be inserted to mouth, the size thereof can be reduced as compared to a conventional arrangement having a transparent container accommodating the image sensor and the light source. Further, since the image is obtained by receiving light reflected by the reflection mirror by the image pick-up optical system, the production cost can be reduced as compared to the conventional image pick-up device having a deflecting device.

The dentition image reading apparatus according to the above aspect of the present invention may preferably have a slant angle adjuster for adjusting a slant angle of the reflection mirror.

Ordinarily, when the slant angle of the reflection mirror relative to perpendicular direction is 45 degrees, the light reflected by right below the upper jaw dentition or right above the lower jaw dentition enters into the image pick-up optical system, whereby the images taken from right below or right above the dentition are synthesized.

According to the above arrangement, since the slant angle adjuster for adjusting the slant angle of the reflection mirror is provided, the obliquely-seen perspective dentition image can be obtained. Therefore, an image seen from the most viewable direction can be obtained even for a dentition of complicated structure.

In the present invention, the image pick-up optical system may preferably include: an image sensor; a lens for forming an image of the light reflected by the reflection mirror on a light-receiving surface of the image sensor; and a light-shield provided between the lens and the reflection mirror for preventing the light from the light source from directly entering into the image sensor.

According to the above arrangement, since the image pick-up optical system has the image sensor and the lens for focusing the light reflected by the reflection mirror on the light-receiving surface of the image sensor and the light-shield is disposed between the lens and the reflection mirror, the light directly entering from the light source into the image sensor can be removed to the utmost, thereby obtaining more vivid image.

In the present invention, the scanner may preferably include: a scanning base supporting the light source and the reflection mirror at a distal end thereof and supporting the image pick-up optical system at a base end thereof; a guide for movably guiding the scanning base along a depth direction of the hollow portion of the in-mouth insert; and a drive unit for moving the scanning base for every predetermined pitch.

According to the above arrangement, since the scanning base having the light source and the reflection mirror at a distal end thereof and having the image pick-up optical system at a base end thereof is movably guided along the depth direction of the hollow portion of the in-mouth insert and is moved for a predetermined pitch by the drive unit, the dentition image in mouth can be accurately obtained for every predetermined pitch.

In the present invention, the in-mouth insert may preferably have the light-transmitting portion respectively on the front and back sides thereof, and the image pick-up optics may preferably include: a light source inserted in the hollow portion in the in-mouth insert for irradiating light on the upper jaw dentition and the lower jaw dentition through the light-transmitting portions; a pair of reflection mirrors for reflecting the light from the upper jaw dentition and the lower jaw dentition toward the outside of the in-mouth insert; a scanner for moving the light source and the pair of reflection mirrors along the depth direction of the hollow portion of the in-mouth insert; and an image pick-up optical system for receiving the light reflected by the pair of reflection mirrors.

According to the above arrangement, since the light-transmitting portions are respectively provided on the front and back sides of the in-mouth insert and the image pick-up optics have the light source inserted in the hollow portion in the in-mouth insert for irradiating light on the upper jaw dentition and the lower jaw dentition through the light-transmitting portions and a pair of reflection mirrors for reflecting the light from the upper jaw dentition and the lower jaw dentition toward the outside of the in-mouth insert, the upper jaw dentition and the lower jaw dentition can be simultaneously taken by a single scan. Further, since the positional relationship between the upper jaw dentition and the lower jaw dentition can be accurately obtained, the positional relationship between the upper and lower bite surfaces can be accurately grasped.

DETAILED DESCRIPTION OF PREFERRED EMBODIMENT(S)

Preferred embodiments of the present invention will be described below with reference to attached drawings. Incidentally, the same reference numeral will be attached to the same components to omit or simplify explanation thereof.

[First Embodiment]

Figure 1:
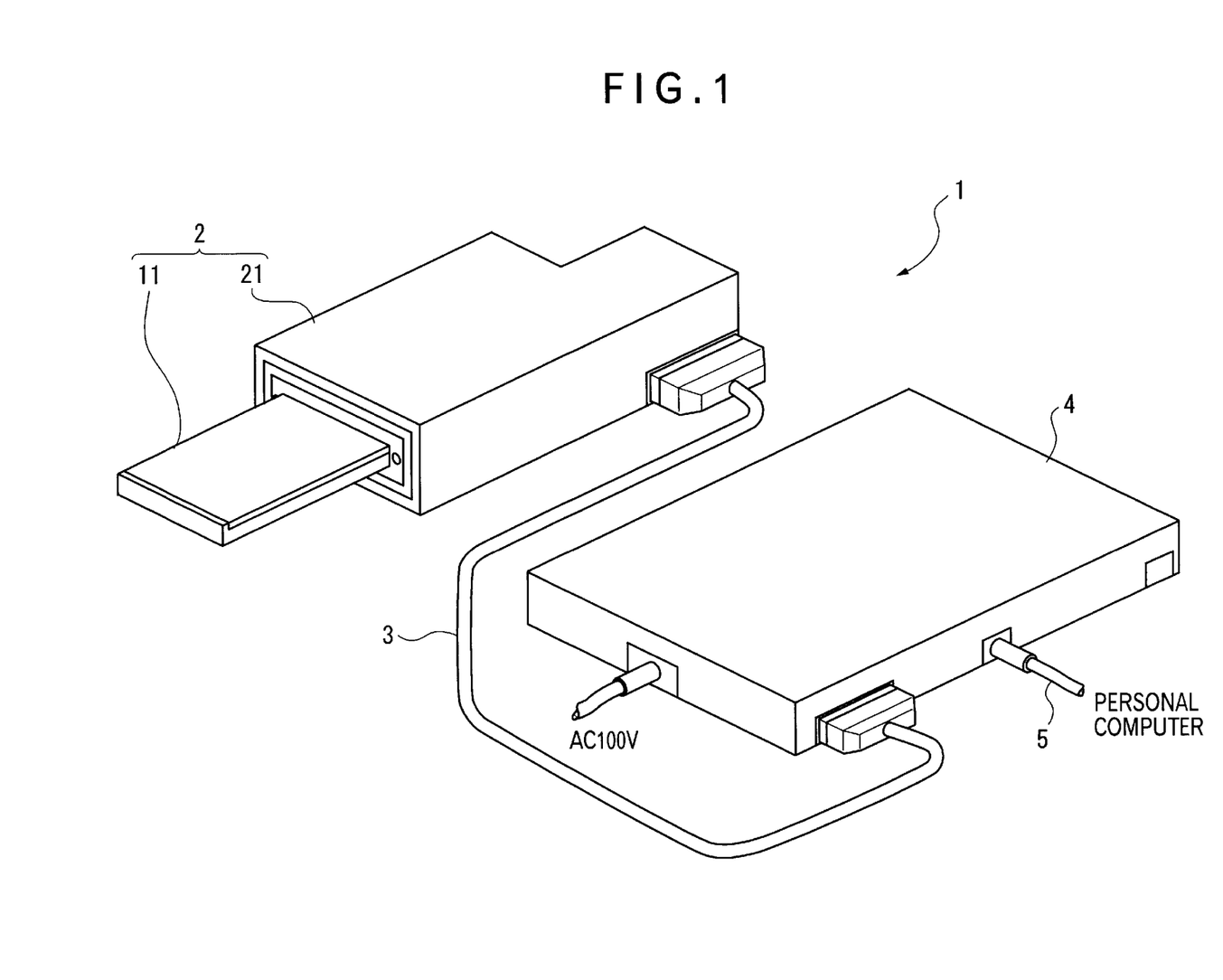
FIG. 1 is an exterior perspective view showing a first embodiment of the present invention.

First embodiment of the present invention is shown in FIGS. 1 to 6. As shown in FIG. 1, the dentition image reading apparatus 1 of the present embodiment includes a dentition image pick-up device 2 and a power source 4 connected to the dentition image pick-up device 2 through a connection cable 3. A personal computer (not shown) constituting a below-described image processing unit is connected to the power source 4 through a USB cable 5.

The dentition image pick-up device 2 includes an in-mouth insert 11 inserted into a mouth having an upper jaw dentition and a lower jaw dentition, and image pick-up optics 21.

Figure 2:
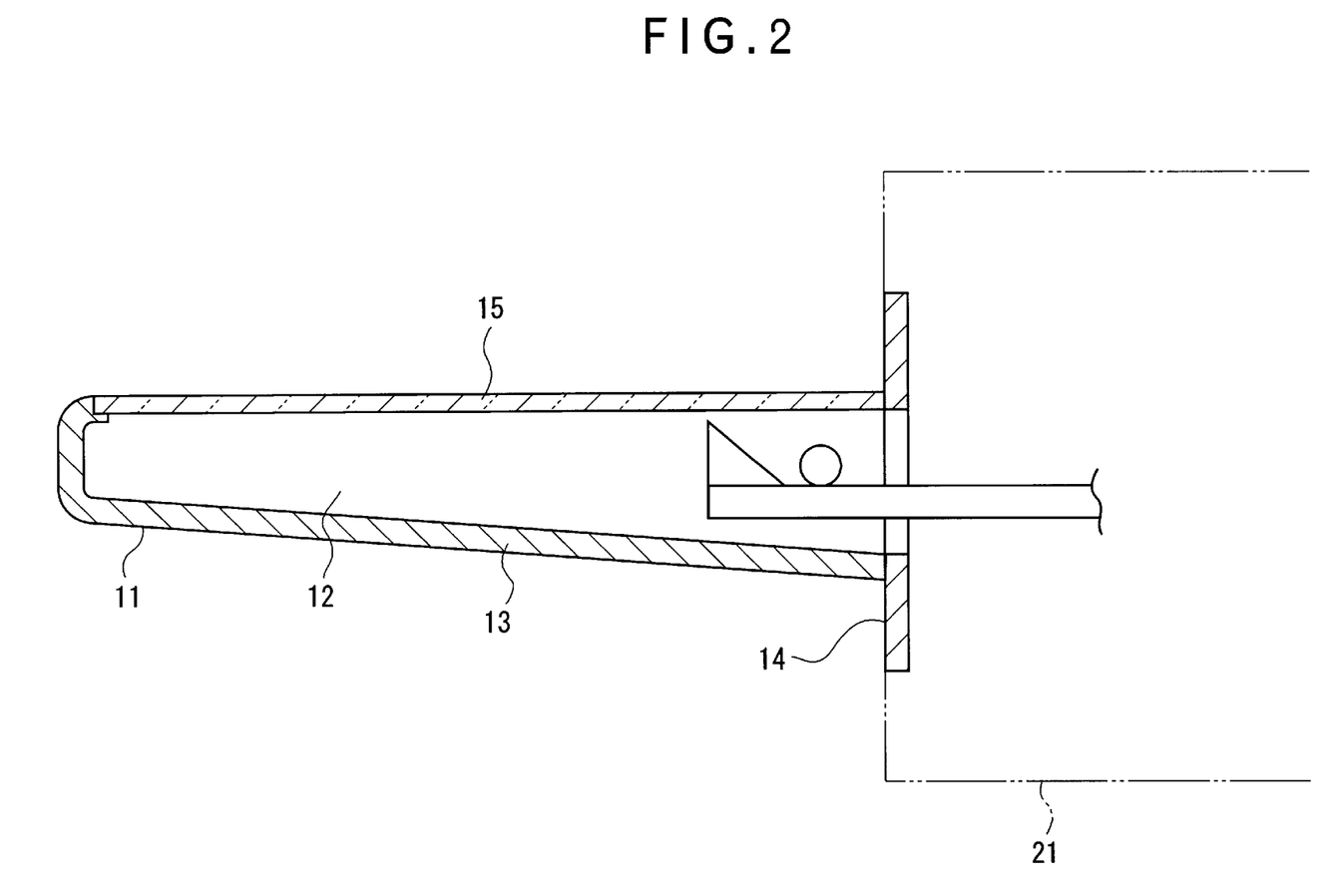
FIG. 2 is a cross section showing an in-mouth insert of the aforesaid embodiment.

As shown in FIG. 2, the in-mouth insert 11 is of width and thickness capable of being inserted into mouth, which includes a flat square insert tube 13 having a hollow portion 12 thereinside and a fringe 14 integrated with the base end of the insert tube 13 and attached to the image pick-up optics 21. A light-transmitting portion 15 is formed at least on one of front and back sides of the insert tube 13, on the upper side here. The light-transmitting portion 15 is formed by attaching a translucent material such as glass on the upper surface of the insert tube 13. Incidentally, the insert tube 13 is formed in a shape with a round corner so as not to damage the inside of the mouth when being inserted into and is made of a material that does not cause unpleasant feeling.

Figure 3:
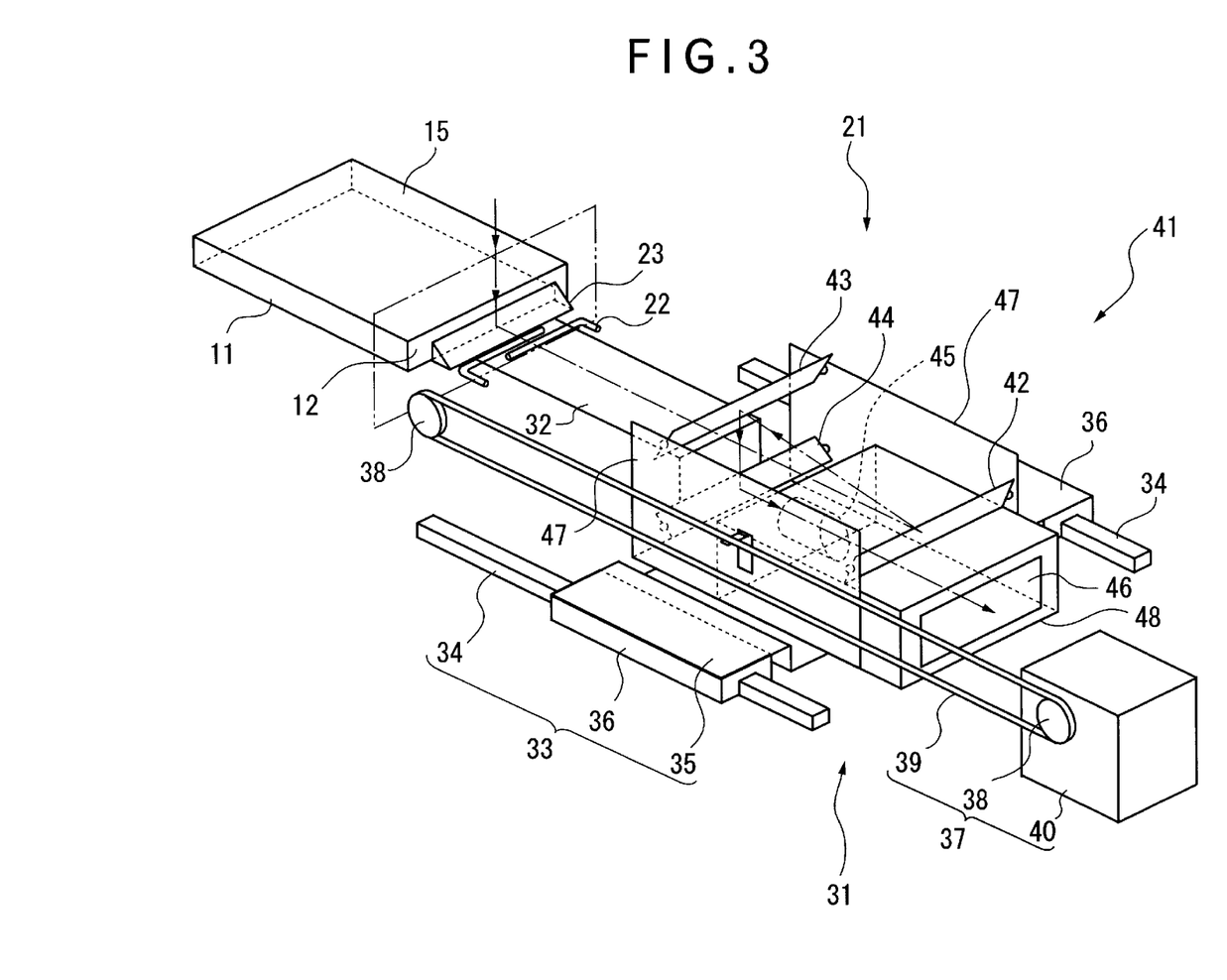
FIG. 3 is perspective view showing an inside of a dentition image pick-up device of the aforesaid embodiment.

As shown in FIG. 3, the image pick-up optics 21 has a cold-cathode tube 22 as a light source inserted in the hollow portion 12 in the in-mouth insert 11 for irradiating light beam onto the dentition through the light-transmitting portion 15, a reflection mirror 23 for reflecting the light beam from the dentition toward the outside of the in-mouth insert 11, a scanner 31 for moving the cold-cathode tube 22 and the reflection mirror 23 along depth direction of the hollow portion 12 in the in-mouth insert 11, and an image pick-up optical system 41 for receiving light reflected by the reflection mirror 23.

The scanner 31 has a scanning base 32 having the cold-cathode tube 22 and the reflection mirror 23 at a distal end thereof and further having the image pick-up optical system 41 at a base end thereof, a guide 33 for movably guiding the scanning base 32 along the depth direction of the hollow portion 12 in the in-mouth insert 11, and a drive unit 37 for moving the scanning base 32 at a predetermined pitch.

The guide 33 is composed of a pair of linear rails 34 provided parallel along the depth direction of the hollow portion 12 in the in-mouth insert 11, and a slider 36 movably provided on the respective rails 34 and connected to the scanning base 32 through a connector 35.

The drive unit 37 includes a pair of pulleys 38 rotatably supported at the front and rear positions in the moving direction of the scanning base 32, a drive belt 39 wound around the pair of pulleys 38 with a part thereof connected with the scanning base 32, and a pulse motor 40 as a drive source for rotating one of the pulleys 38.

Figure 4:
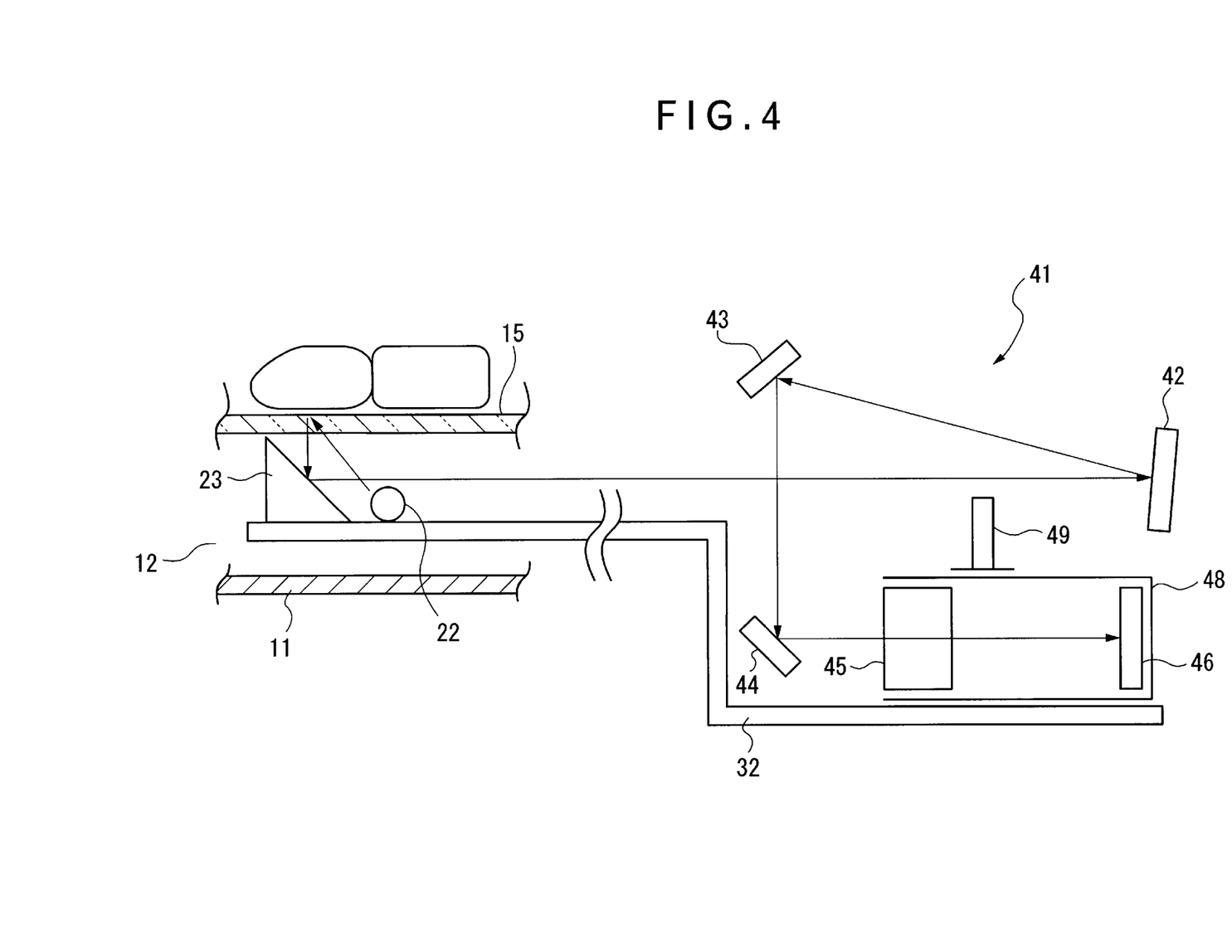
FIG. 4 is an illustration showing an image pick-up optical system of the aforesaid embodiment.

As shown in FIG. 4, the image pick-up optical system 41 includes a mirror 42 for reflecting the light reflected by the reflection mirror 23 toward obliquely upper front, a mirror 43 for reflecting the light reflected by the mirror 42 directly downward, a mirror 44 for backwardly reflecting the light reflected by the mirror 43, and a lens 45 for focusing the light reflected by the mirror 44 on a light-receiving surface of a color CCD 46 as an image sensor. The mirrors 42, 43 and 44 are held by a pair of mirror holders 47 vertically extending from both sides of the scanning base 32. The lens 45 and the color CCD 46 are accommodated in a tube-shaped lens holder 48. A light-shield 49 for preventing the light from the cold-cathode tube 22 from directly entering onto the color CCD 46 is provided on the upper surface of the lens holder 48. Incidentally, a color line image sensor is used as the color CCD 46.

Figure 5:
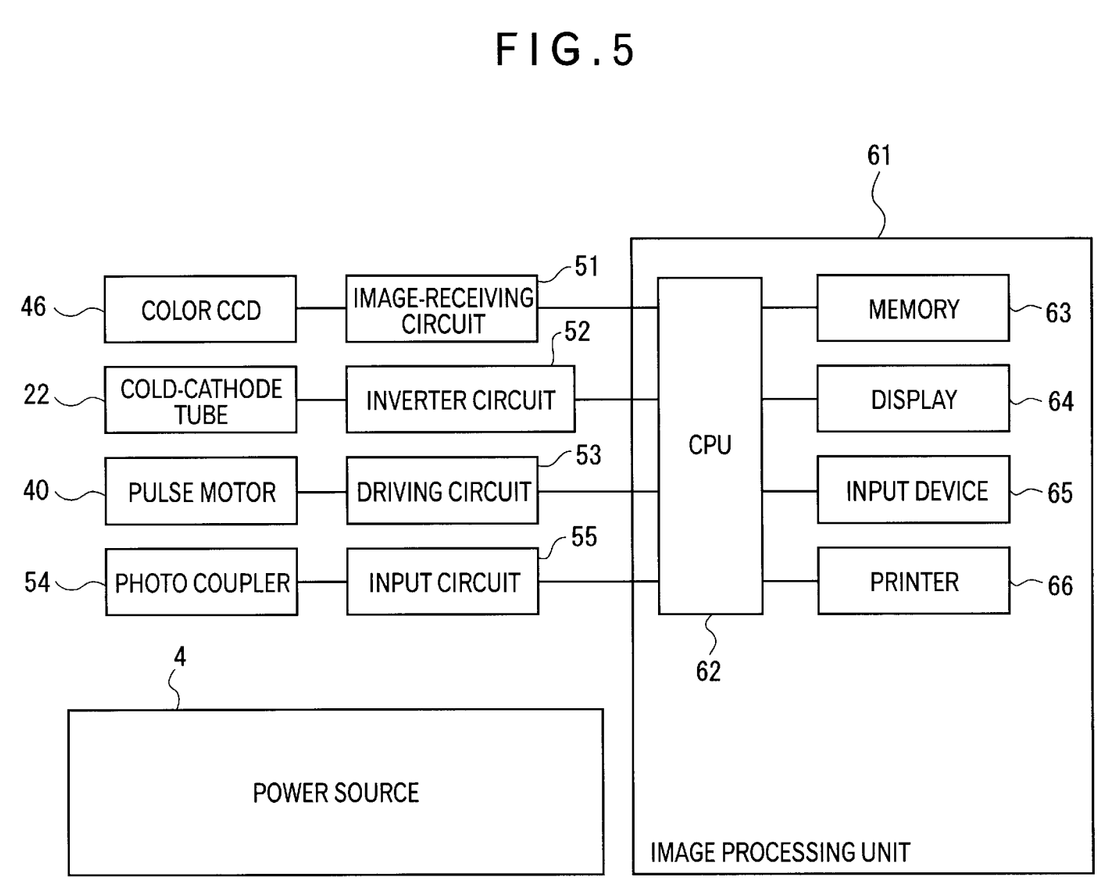
FIG. 5 is an illustration of a control block of the aforesaid embodiment.

FIG. 5 shows a control block of the present embodiment. In the figure, a line of image data is retrieved by the color CCD 46, which is converted into a digital signal and is inputted to a CPU 62.

The cold-cathode tube 22 is driven by an inverter circuit 52 and electric current thereto is adjusted by an illumination-intensity command from the CPU 62.

The pulse motor 40 feeds for one step through a drive circuit 53 in accordance with a command from the CPU 62. The movement of the scanning base 32 is set, for instance, for 0.02 mm/step.

A photo coupler 54 is used for detecting origin of the scanning base 32, which is inputted to the CPU 62 via an input circuit 55 as an origin signal.

The power source 4 supplies power source necessary for the inverter circuit 52 and the drive circuit 53.

The image processing unit 61 includes the CPU 62, a memory 63, a display 64, an input device 65 and a printer 66, which is arranged in a personal computer (not shown). The memory 63 is constructed by an internal memory or an external storage (e.g. floppy disk and MO). A CRT and a liquid crystal display is used as the display 64. The input device 65 is constructed from a measurement initiation button, measurement cancel button, origin return button and an illumination button as well as a keyboard and a mouse.

Next, a using method of the present embodiment will be described below.

Initially, when it is commanded to return to the origin, the scanning base 32 is positioned to an imaging initiating position (the most retracted position of the scanning base 32=origin position) by the pulse motor 40.

Next, when the measurement is initiated, the pulse motor 40 is driven for one step and, after being stopped, a one-line color image data is outputted from a color CCD 46, which is stored in the memory 63 through the image-receiving circuit 51 and the CPU 62. Subsequently, the pulse motor 40 is again driven for one step and another one-line color image data is outputted from the color CCD 46, which is stored on another area of the memory 63 through the image-receiving circuit 51 and the CPU 62. When the operation is sequentially repeated and the scanning base 32 reaches a imaging termination position (the most protruded position of the scanning base 32), the imaging process is terminated and the scanning base 32 returns to the origin.

Figure 6:
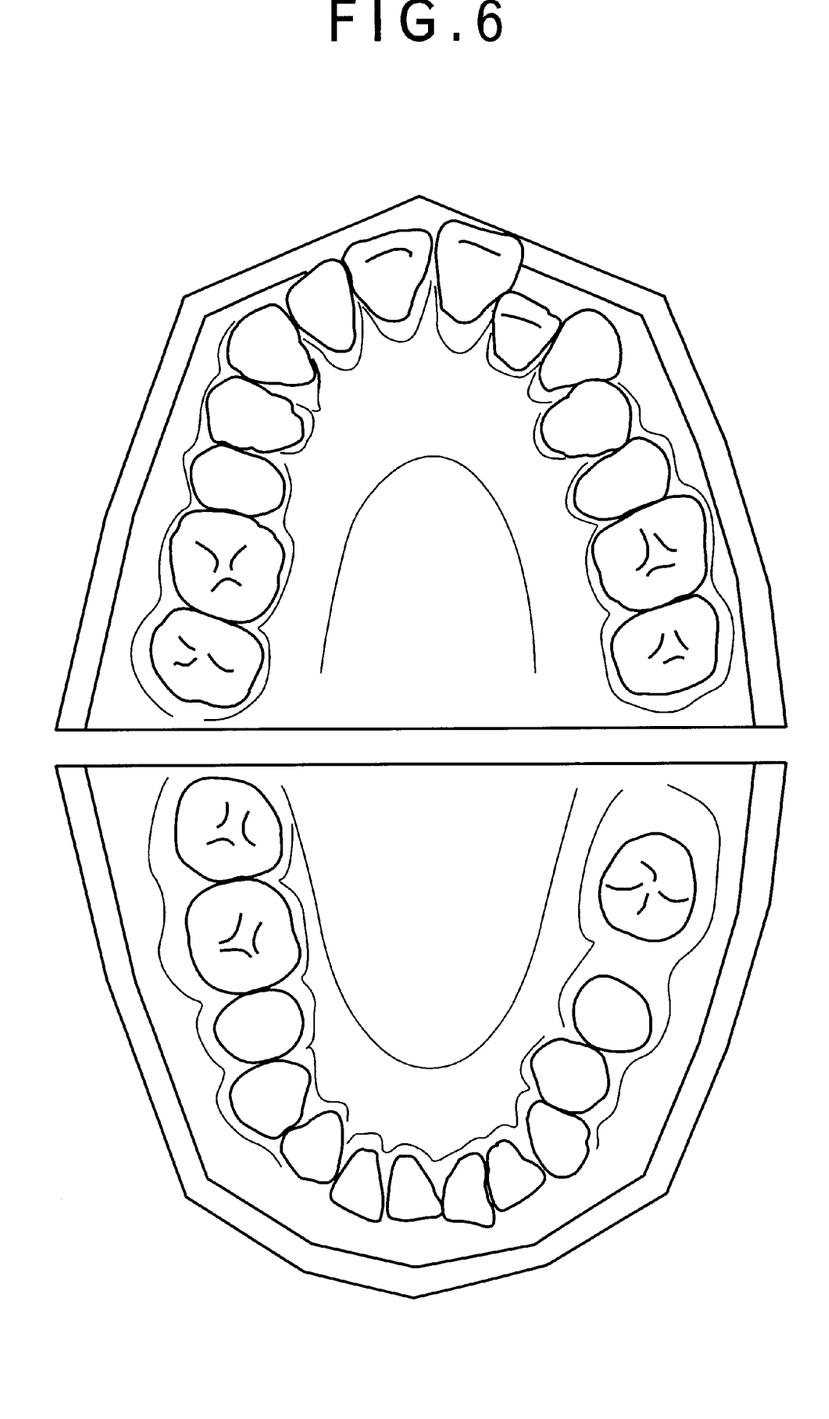
FIG. 6 is an illustration of the image of the dentition taken by the aforesaid embodiment.

The color image data of respective lines is combined to be an image of the entire dentition and the result is either displayed on the display 64 or printed out from the printer 66. For instance, as shown in FIG. 6, the image of the entire dentition is displayed or printed out. Though both of the upper jaw dentition and the lower jaw dentition are displayed in the figure, only one of the images ordinarily can be obtained by one scan. Accordingly, after obtaining the image of the upper dentition by the first scan, the second scan may be conducted with the dentition image pick-up device 2 upside down, thereby obtaining the image of the lower jaw dentition.

Incidentally, the image is stored in the other area of the memory 63 or in the external storage as necessary. Alternatively, the data may be transmitted to the other analyzer through a wire or wireless communication line.

According to the present embodiment, since the image of the entire dentition taken from right below the dentition or right above the dentition can be read with a high resolution, accurate dimension of the tooth or between the teeth can be measured. Incidentally, since the image is taken with a resolution of 1200 dpi, one pixel of the image corresponds to 0.02 mm in terms of dimension. Since the dimension can be measured with high resolution, for instance, artificial tooth may be made with accurate dimension.

Since only the cold-cathode tube 22 as a light source and the reflection mirror 23 are provided in the hollow portion 12 of the in-mouth insert 11 inserted in mouth, the size of the apparatus can be reduced as compared to a conventional arrangement having a transparent container accommodating an image sensor and a light source. Further, since the light reflected by the reflection mirror 23 is received by the image pick-up optical system 41 to obtain an image, the production cost can be reduced as compared to a conventional mage pick-up device having a deflecting device.

Since the image pick-up optical system 41 includes the color CCD 40 and the lens 45 for focusing the light reflected by the reflection mirror 23 onto the light-receiving surface of the color CCD 40 and the light-shield 49 is disposed between the lens 45 and the reflection mirror 23, the light directly entering into the color CCD 40 from the cold-cathode tube 22 can be diminished to the utmost, thereby obtaining more vivid dentition image.

Further, since the scanning base 32 having the cold-cathode tube 22 and reflection mirror 23 at a distal end thereof and the image pick-up optical system 41 at a base end thereof is movably guided in the depth direction of the hollow portion 12 of the in-mouth insert 11 and is moved by a predetermined pitch by the drive unit 37, the dentition image for the predetermined pitch can be accurately retrieved in mouth.

[Second Embodiment]

Figure 7:
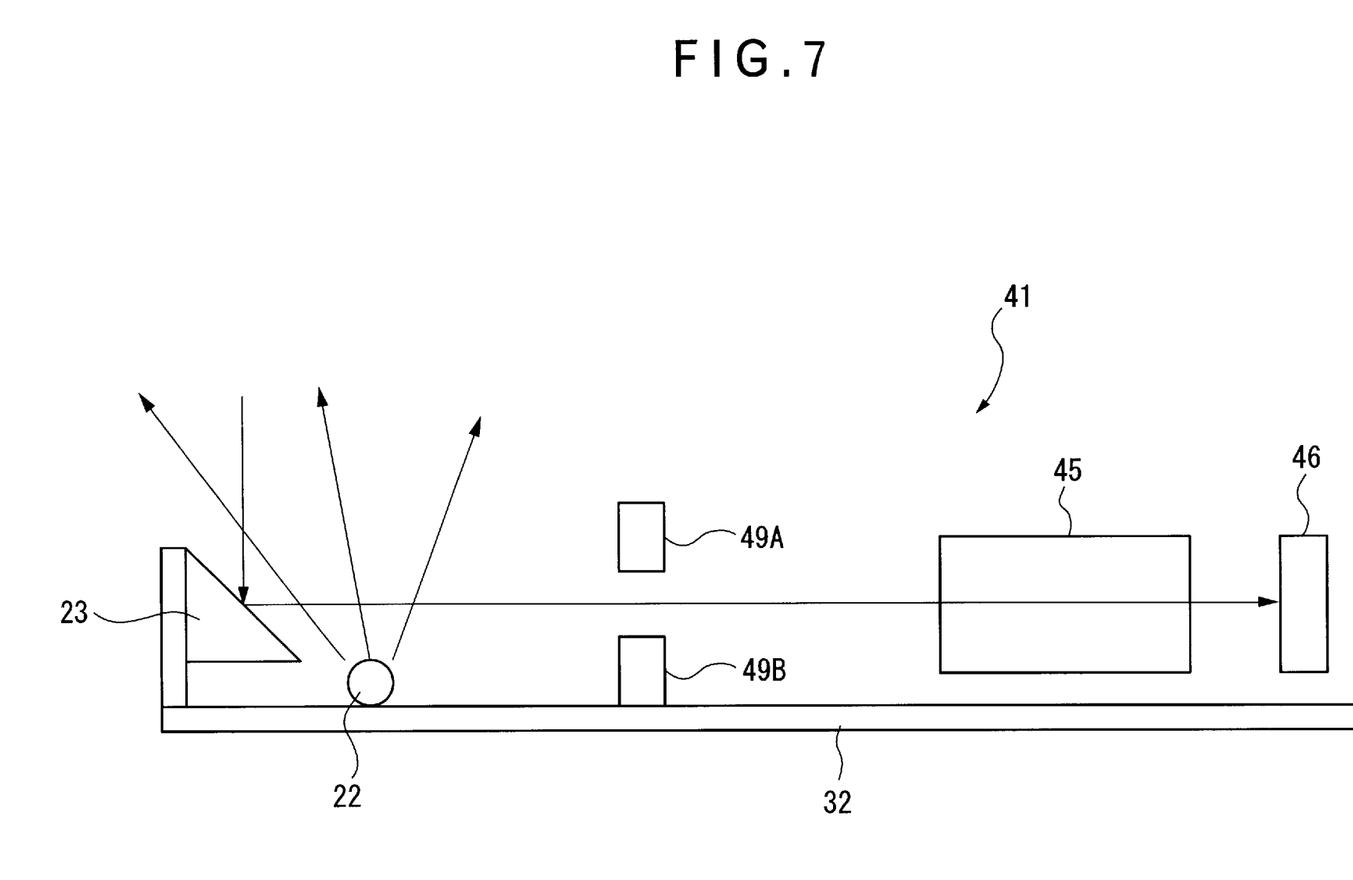
FIG. 7 is an illustration showing a second embodiment of the present invention.

FIG. 7 shows a second embodiment. The dentition image reading apparatus according to the present embodiment has shorter light path length than the first embodiment by shortening the focus distance of the lens 45, thereby omitting mirrors 42, 43 and 44.

Further, the present embodiment differs from the first embodiment in that the two light-shield plates 49A and 49B are disposed sandwiching the light path between the reflection mirror 23 and the lens 45.

[Third Embodiment]

Figure 8:
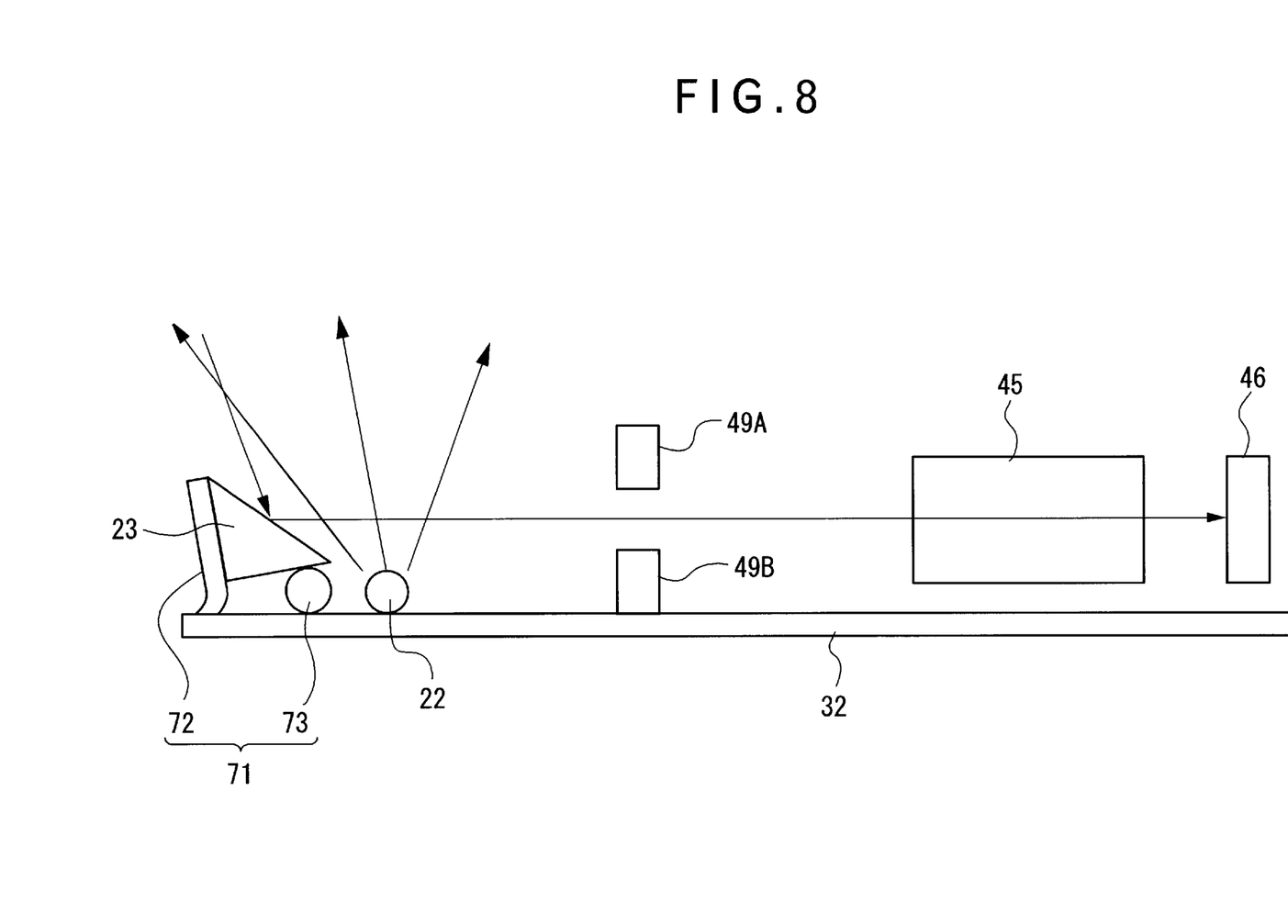
FIG. 8 is an illustration showing a third embodiment of the present invention.

FIG. 8 shows a third embodiment. The dentition image reading apparatus of the present embodiment differs from the second embodiment in that a slant angle adjuster 71 for adjusting the slant angle of the reflection mirror 23 is added.

The slant angle adjuster 71 is composed of a leaf spring 72 cut and raised from the scanning base 32 and attached with the reflection mirror 23, and an inclination adjuster 73 movable toward and away from the leaf spring 72 provided between the reflection mirror 23 and the scanning base 32.

According to the above arrangement, when the inclination adjuster 73 is moved toward and away from the leaf spring 72, the leaf spring 72 is bent in accordance with the position thereof, thus changing the slant angle of the reflection mirror 23. Then, though the light reflecting right below or just above the dentition enters into the color CCD 46 through the reflection mirror 23 in the conventional arrangement, the light reflected by the other angle can enter into the color CCD 46 through the reflection mirror 23, so that a perspective dentition image seeing the dentition from an oblique angle can be obtained. Accordingly, an image taken from most suitable direction (angle) can be taken even for a complex dentition.

In the dentition image reading apparatus of the present embodiment, the color image data from right below the dentition (or right above the dentition) for each one line may be obtained from the image pick-up initiation position of the scanning base 32 to the image pick-up termination position as in the first embodiment, and, subsequently, the color image data for each one line may be obtained by inclining the reflection mirror 23 from the image pick-up termination position to the image pick-up initiation position. Accordingly, the entire dentition image from right below the dentition can be obtained by scanning from front side toward depth side of the mouth and, further, a perspective dentition image can be obtained by return-scanning from the depth side toward the front side of the mouth.

Though the position of the inclination adjuster 73 is manually adjusted in the present embodiment, the position may be adjusted from the outside using the other controller such as solenoid. Further, though the reflection mirror 23 is inclined backward, the reflection mirror 23 may be inclined forward.

[Fourth Embodiment]

Figure 9:
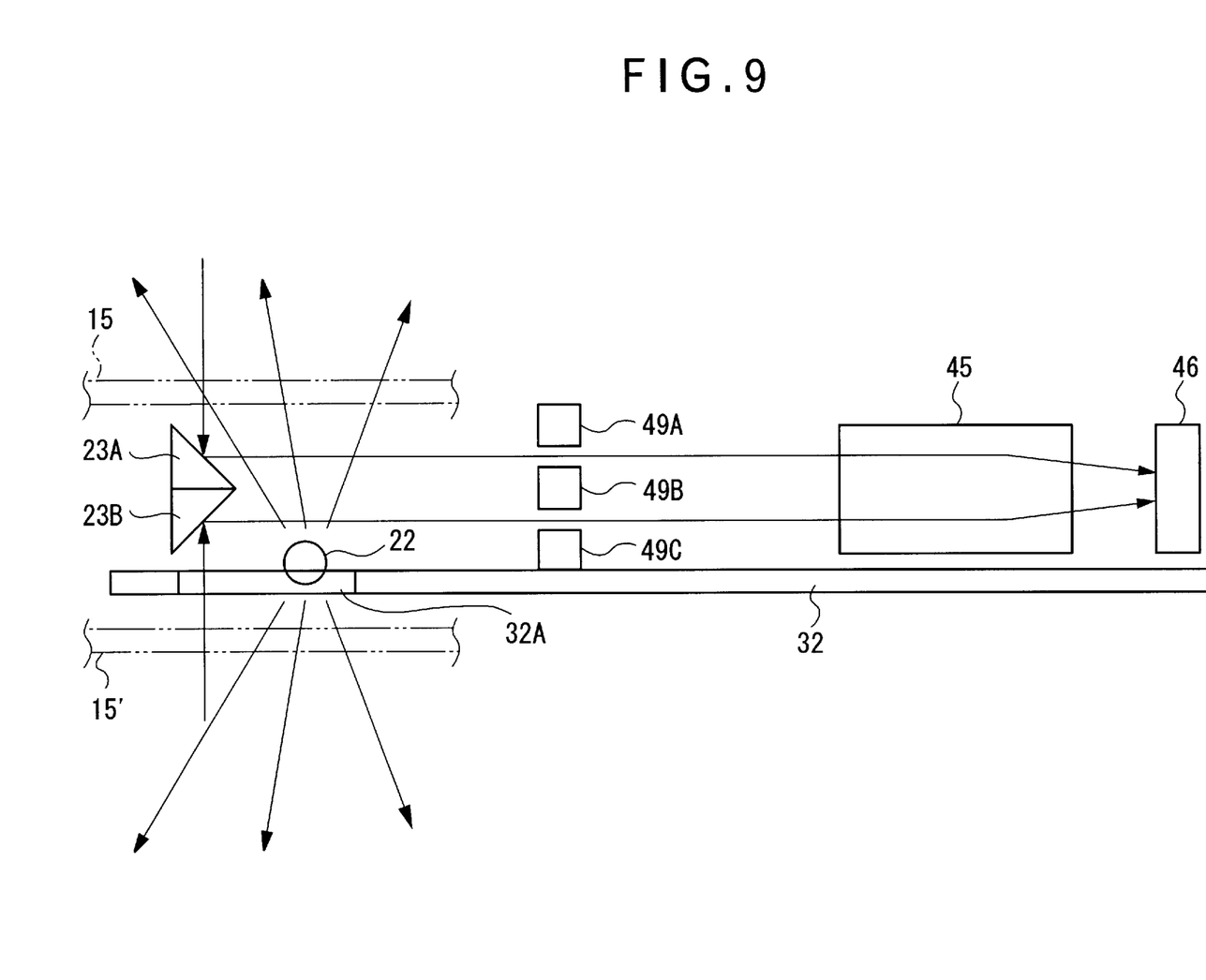
FIG. 9 is an illustration showing a fourth embodiment of the present invention.

FIG. 9 shows a fourth embodiment. The dentition image reading apparatus of the present embodiment is arranged so that the image of the upper jaw dentition and the lower jaw dentition can be simultaneously taken by a single scan.

Specifically, light-transmitting portions 15 are formed on the top and bottom sides, i.e. upper and lower surfaces of the in-mouth insert 11 and a notch 32A is formed on the scanning base 32 extending on the entire scan range. The image pick-up optical system 41 includes a pair of reflection mirrors 23A and 23B for reflecting the light from the upper jaw dentition and the lower jaw dentition toward the outside of the in-mouth insert 11.

The color CCD 46 is not a color line sensor but a two-dimensional color CCD array for simultaneously taking image of the two reflection lights, where two-line data of specific line are used for the upper jaw dentition and the lower jaw dentition.

According to the present embodiment, the image of the upper jaw dentition and the lower jaw dentition can be simultaneously taken by a single scan and the positional relationship of the upper jaw dentition can the lower jaw dentition can be accurately obtained, so that the positional relationship between the upper and lower bite surfaces can be accurately grasped.

Though three light-shields 49A, 49B and 49C are used in the present embodiment, the intermediate light shield 49B may be omitted when the two reflection lights are close.

[Other Embodiments]

Incidentally, following modifications and applications of the present invention are possible as well as the above-described embodiments.

For instance, though the light-shield is provided for preventing the illumination light from the cold-cathode tube 22 from directly entering into the color CCD 46 in the respective embodiments, the light shield may be provided on the front and rear sides (right and left sides in FIGS. 4, 7 and 9) of the cold-cathode tube 22 in order to prevent the light reflected by the reflection mirror 23 or other generated stray light.

The pulse motor 40 is used to drive the scanning base 32 and the drive of the pulse motor 40 and the image pick-up by the color CCD 46 are alternately conducted in the above embodiments. However, the scanning base 32 may be continuously moved from the image pick-up position to the image pick-up termination position using a motor of other type (ex. direct-current motor) of which linear scale output is monitored to obtain the output of the color CCD 46 composed of the line image sensor for a predetermined distance (0.02 mm for instance).

At this time, absolute-type scale may be used as the linear scale in order to omit the origin switch.

The image pick-up initiation position and the image pick-up termination position may be arranged so that the image pick-up initiation position is located at a position for the scanning base 32 to be most protruded (deepest part in mouth) and the image pick-up termination position may be located where the scanning base 32 is the most retracted.

The light source is not limited to the cold-cathode tube 22, but may be a LED of, for instance, white color or a halogen lamp. In this arrangement, a dimmer circuit may be used instead of the inverter circuit, thereby simplifying the construction of the circuit.

Not only USB cable but also SCSI interface or GPIB interface may be used between the personal computer and the power source 4, and any interface cable may be used for appropriate connection with the personal computer.

What is claimed is:

1. A dentition image reading apparatus, comprising:
   an in-mouth insert to be inserted in a mouth having an upper jaw dentition and a lower jaw dentition; and image pick-up optics,
   the in-mouth insert having a light-transmitting portion at least on one of front and back sides thereof and a hollow portion provided thereinside,
   the image pick-up optics having: a light source inserted in the hollow portion in the in-mouth insert for irradiating light on the dentition through the light-transmitting portion; a reflection mirror for reflecting the light from the dentition toward the outside of the in-mouth insert; a scanner for moving the light source and the reflection mirror along the depth direction of the hollow portion of the in-mouth insert; and an image pick-up optical system for receiving the light reflected by the reflection mirror; and wherein the light source irradiates light directly on the dentition.

2. The dentition image reading apparatus according to claim 1, further comprising a slant angle adjuster for adjusting a slant angle of the reflection mirror.

3. The dentition image reading apparatus according to claim 1, the image pick-up optical system comprising: an image sensor; a lens for forming an image of the light reflected by the reflection mirror on a light-receiving surface of the image sensor; and a light-shield provided between the lens and the reflection mirror for preventing the light from the light source from directly entering into the image sensor.

4. The dentition image reading apparatus according to claim 1, the scanner comprising: a scanning base supporting the light source and the reflection mirror at a distal end thereof and supporting the image pick-up optical system at a base end thereof; a guide for movably guiding the scanning base along a depth direction of the hollow portion of the in-mouth insert; and a drive unit for moving the scanning base for every predetermined pitch.

5. The dentition image reading apparatus according to claim 1, wherein the in-mouth insert has the light-transmitting portion respectively on the front and back sides thereof, and wherein the image pick-up optics include: a light source inserted in the hollow portion in the in-mouth insert for irradiating light on the upper jaw dentition and the lower jaw dentition through the light-transmitting portions; a pair of reflection mirrors for reflecting the light from the upper jaw dentition and the lower jaw dentition toward the outside of the in-mouth insert; a scanner for moving the light source and the pair of reflection mirrors along the depth direction of the hollow portion of the in-mouth insert; and an image pick-up optical system for receiving the light reflected by the pair of reflection mirrors.

* * * * *